United States Patent
Petersen

(10) Patent No.: US 7,658,813 B2
(45) Date of Patent: Feb. 9, 2010

(54) METHOD OF PREPARING CLOSURE COMPONENTS SUITABLE FOR USE IN DIAPERS

(75) Inventor: Johann F. Petersen, Grevenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 377 days.

(21) Appl. No.: 10/545,976

(22) PCT Filed: Feb. 12, 2004

(86) PCT No.: PCT/US2004/004533

§ 371 (c)(1), (2), (4) Date: Aug. 18, 2005

(87) PCT Pub. No.: WO2004/078086

PCT Pub. Date: Sep. 16, 2004

(65) Prior Publication Data

US 2006/0271004 A1 Nov. 30, 2006

(30) Foreign Application Priority Data

Feb. 28, 2003 (EP) .................................. 03004500

(51) Int. Cl.
B32B 38/04 (2006.01)
A61F 13/15 (2006.01)
(52) U.S. Cl. ........................ 156/253; 156/250; 156/252; 604/386; 604/389; 604/390; 604/391
(58) Field of Classification Search .................. 156/250, 156/252, 253; 604/389–391, 385.01, 385.03, 604/385.04, 386
See application file for complete search history.

(56) References Cited

U.S. PATENT DOCUMENTS 5,399,219 A * 3/1995 Roessler et al. ............. 156/259
5,487,809 A * 1/1996 Goulait et al. .............. 156/259

(Continued)

FOREIGN PATENT DOCUMENTS

JP 11-181374 7/1999
JP 2002-45214 2/2002

*Primary Examiner*—Mark A Osele
*Assistant Examiner*—Christopher C Caillouet
(74) *Attorney, Agent, or Firm*—Kathleen B. Gross; William J. Bond

(57) ABSTRACT

A method of preparing closure components and a method of preparing a stable roll of such components. The methods include (a) providing a fastening portion comprising fastening means; (b) providing a continuous web of a material in a machine direction, said web having a first outer major surface and a second inner major surface and a left and right longitudinal edge at least one of said first and second major surfaces being capable of releasably engaging with the fastening means; (c) joining said fastening portion in the machine direction to the inner and/or outer major surfaces of the web so that the fastening means of said fastening portion are exposed; applying at least two first cuts to the web in order to provide at least two flaps each having a top edge and a baseline, each of said at least two first cuts being discontinuous in the machine direction and in a cross direction, each of said at least two flaps bearing at least part of said fastening portions and being connected to the web at least through its respective baseline so that the baselines of said at least two flaps face opposite longitudinal edges of the web; (e) folding over the flaps into a direction from their top edges to their baseline essentially along said base line onto the web so that the fastening means releasably engage with the first outer major surface or the second inner major surface of the web. A closure component and a stable roll made according to the methods are also disclosed.

17 Claims, 6 Drawing Sheets

U.S. PATENT DOCUMENTS

| | | | | |
|---|---|---|---|---|
| 5,705,013 A | * | 1/1998 | Nease et al. | ................ 156/260 |
| 5,759,317 A | | 6/1998 | Justmann | |
| 6,051,094 A | | 4/2000 | Melbye et al. | |
| 6,406,468 B1 | | 6/2002 | Dilnik et al. | |
| 6,428,526 B1 | | 8/2002 | Heindel et al. | |
| 6,620,147 B2 | | 9/2003 | Shingu et al. | |

* cited by examiner

METHOD OF PREPARING CLOSURE COMPONENTS SUITABLE FOR USE IN DIAPERS

FIELD OF THE INVENTION

The present invention relates to a method of preparing closure components suitable for use in disposable absorbent articles and to a stable roll comprising a sequence of pre-formed closure components which are obtainable by said method.

BACKGROUND OF THE INVENTION

Disposable absorbent articles comprise diapers but also other absorbent articles such as incontinence briefs, diaper holders, feminine hygiene garments, training pants, panties, underpants and the like.

Such disposable absorbent articles typically comprise closure components which are used to safely secure the absorbent article to the body of the wearer. The fastening means employed in such closure components include, for example, adhesive means such as pressure-sensitive adhesive means but mechanical fastening means are also used. In the case of mechanical fastening means, the closure component typically comprises at least a first component of such fastening means which is capable of engaging with at least a second matching component of said fastening means arranged at another part of the absorbent article. Mechanical fastening means include, for example, mechanical hooks as a first male component and a fibrous material as a second mating female component.

Disposable absorbent articles often employ materials such as woven or non-woven materials having an exposed surface providing a cloth-like feeling in order to increase the comfort of wearing. It was found that the closure components and, in particular, mechanical closure components tend to engage with such surfaces during the manufacturing of the absorbent articles in an uncontrolled way which may adversely affect subsequent steps of the process of manufacturing.

U.S. Pat. No. 6,428,526 discloses a process for attaching and protecting a mechanical fastener material on a disposable absorbent article. The process includes applying a continuous hook material to a substrate web and cutting by a cutter to form individual fastening portions whereby a substantial part of the substrate web bearing the hook material is discarded. The fastening portions are then folded over and releasably engaged.

U.S. Pat. No. 5,759,317 discloses a method of forming a plurality of closure components which comprises providing a composite web which includes a web of hook material. The composite web is divided along first and second, non-intersecting, continuous serpentine division lines which repeatedly traverse across a complete lateral width of the hook web and extend generally longitudinally along a medial region of the composite thus providing a serpentine strip which needs to be discarded. The method according to US '317 does furthermore not allow for a wide variation of the shape of the closure components obtained.

An overriding consideration in the construction of absorbent articles is the cost of manufacturing which includes— besides running the process of manufacturing at high speed and with high reliability—also the requirement of minimizing waste.

It is therefore an object of the present invention to provide a cost-effective method of manufacturing closure components suitable for use in disposable absorbent articles such as diapers which is characterized by a high reliability and can be run at high speed with a reduced amount of waste. Other objects of the present invention can be taken from the following detailed description.

BRIEF DESCRIPTION OF THE INVENTION

The present invention refers to a method of preparing closure components suitable for use in absorbent articles such as diapers, comprising the steps of providing a fastening portion comprising fastening means; providing a continuous web of a material in a machine direction, said web having a first outer major surface and a second inner major surface and a left and right longitudinal edge, at least one of said first and second major surfaces being capable of releasably engaging with the fastening means; joining said fastening portion in the machine direction to the inner and/or outer major surfaces of the web so that the fastening means of said fastening portion are exposed; applying at least two first cuts to the web in order to provide at least two flaps each having a top edge and a baseline, each of said at least two first cuts being discontinuous in the machine direction and in a cross direction, each of said at least two flaps bearing at least part of said fastening portions and being connected to the web at least through its respective baseline so that the baselines of said at least two flaps face opposite longitudinal edges of the web; folding over the flaps into a direction from their top edges to their baseline essentially along said base line onto the web so that the fastening means releasably engage with the first outer major surface or the second inner major surface of the web, and applying further cuts to the web to produce individual closure components comprising said flaps in a folded position, wherein the first and further cuts are applied so that the waste w which is defined as $$1-(\text{sum of surface area of the closure components with the flaps being in an unfolded position/surface area of the continuous web})$$

is less than 0.2. The sum of the surface area of the flaps 5 is measured in their unfolded, i.e. not folded-over state, and the area of the continuous web is measured prior to applying any cuts 4, 4', 4".

The present invention furthermore refers to a method of preparing a stable roll comprising a sequence of pre-formed closure components suitable for use in absorbent articles such as diapers, in machine direction, said method comprising the steps of providing a fastening portion; providing a continuous web of a material in a machine direction, said web having a first outer major surface and a second inner major surface and a left and right longitudinal edge, at least one of said first and second major surfaces being capable of engaging releasably with the fastening means; joining said fastening portion in the machine direction to the inner and/or outer major surfaces of the web so that the fastening means are exposed; making at least two cuts in the web in order to provide at least two flaps each having a top edge and a baseline, each of said at least two flaps bearing at least part of said fastening portion, and being connected to the web at least through its baseline so that the baselines of at least two of said flaps face opposite longitudinal edges of the web; folding over the flaps into a direction from their top edges to their baseline essentially along said base line onto the web so that the fastening means releasably engage with the surface of the web, and winding up the web into a roll.

The present invention furthermore refers to a stable roll comprising a sequence of pre-formed closure components suitable for use in diapers, said roll comprising a continuous web of a material in machine direction having a first outer major surface and a second inner major surface and a left and right longitudinal edge, said web bearing fastening portions and at least two flaps each having a top edge and a baseline, each of the flaps bearing at least part of said fastening portions and being connected to the web at least through its respective baseline so that the baselines of said at least two flaps face opposite longitudinal edges of the web, said flaps being folded over into a direction from their top edges to their baseline essentially along said base line onto the web so that the fastening means 3 are in releasable engagement with the corresponding surface 1a, 1b of the web 1.

The invention also relates to a closure component suitable for being attached to absorbent articles, said closure component comprising a base and at least two flaps each of said flaps having a top edge and a baseline and bearing at least part of a fastening portion having fastening means, each of said flaps being connected to the base at least through its respective baseline, said base having a first outer major surface and a second inner major surface at least one of which being capable of releasably engaging with the fastening means of the fastener portions of the flaps.

The invention furthermore refers to the use of said closure component comprising at least two flaps in adult incontinence products.

BRIEF DESCRIPTION OF THE FIGURES

In FIG. 5a the flaps 5 are in the folded-over position whereas the flaps 5 are unfolded in FIG. 5b and ready to be engaged to the landing zone 14.

DETAILED DESCRIPTION OF THE INVENTION

As used above and below, the term "absorbent article" refers to articles which are placed against or in proximity of the body of the wearer to absorb and contain the various exudates discharged from the body. The absorbent article preferably is disposable, i. e. it is intended to be disposed after single use and not intended to be laundered or otherwise restored or reused.

Examples of disposable absorbent articles include diapers, adult incontinence products, training pants, feminine napkins, wound dressings and the like.

A preferred embodiment of the absorbent article referred to in the present invention is a diaper. The term "diaper" as used above and below refers to a garment generally worn by infants or incontinent persons that is drawn up between the legs and fastened about the waist of the wearer.

Figure 5A:
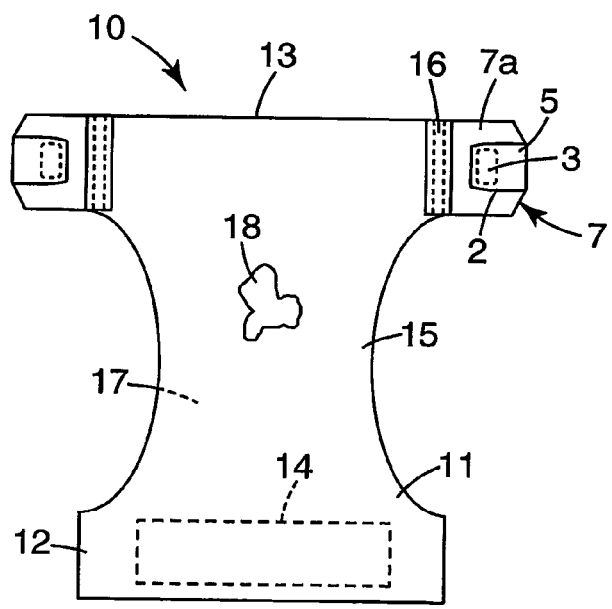
FIGS. 5a and 5b schematically show a diaper 10 comprising a rear waistband section 13, a front waistband section 12 and an intermediate crotch section, the closure components 7 being laterally applied to the rear waistband section 13.

Diapers 10 may have any desired shape such as, for example, a rectangular shape, an I shape, a T shape or an essentially hour-glass shape the latter being schematically shown in FIGS. 5a) and b). The diaper 10 typically has a rear waistband section 13, a front waistband section 12 and an intermediate crotch section 15 which interconnects the rear and front waistband sections 12, 13.

Figure 5B:
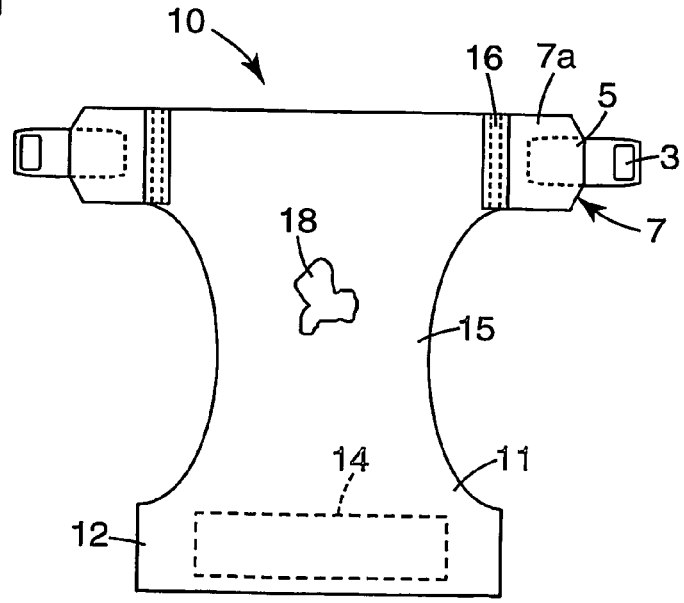

The diaper 10 comprises a top sheet 11 contacting the wearer's skin, a backsheet 17 onto which the landing zone 14 shown in FIG. 5a, 5b in dotted lines is attached facing outwards and an absorbent core 18 (schematically indicated in FIG. 5) sandwiched between said top sheet 11 and back sheet 17.

The diaper 10 comprises closure components 7 which are usually anchored at the seam sections 16 to the lateral edges of the rear waistband section 13. The closure component 7 can be joined to only one of the back sheet 17 and the top sheet 11 but it is often preferred that the closure components are joined to both the top sheet 11 and the back sheet 17 in order to provide a secure and reliable anchoring. Alternatively, the closure component 7 can also be joined to the diaper in between the top sheet 11 and the back sheet 17.

The closure component 7 can be joined to the diaper 10 by various means comprising, for example, pressure-sensitive adhesives, hot melt adhesives or other adhesives, by ultrasonic bonding, thermal bonding applying heat and pressure, by mechanical bonding, stitching or any combination of these bonding methods. The closure component 7 comprises a fastening portion 2 having fastening means 3 which during the use of the diaper typically engage with the landing zone 14 on the back sheet side of the front waistband section 12 in order to secure the waistband sections 12, 13 of the diaper 10 around the wearer. The fastening portion 2 forms part of the flap 5 which is folded onto the inner surface 1a of the closure component in FIG. 5a and which is unfolded in FIG. 5b.

The above description of the diaper 10 is meant to be explanatory only and not limiting. Further details on diapers and their construction can be taken, for example, from EP 0,669,121, EP 0,888,101 and U.S. Pat. No. 6,428,526.

The present invention relates to a novel method of preparing closure components suitable for use in absorbent articles and, in particular, diapers 10.

In a first step of the method of the present invention a continuous web 1 of a material is supplied which continuously extends in the machine direction (MD) and has two longitudinal edges 1c, 1d extending essentially in such machine direction. The continuous web exhibits a first outer major surface 1b and a second inner major surface 1a.

The term "machine direction" (MD) as used above and below denotes the direction of the running, continuous web 1 of a material during the manufacture of the closure components. In the embodiment of the continuous web 1 shown in FIG. 1, the machine direction (MD) corresponds to the direction of the longitudinal edges of the web 1. The term "cross-direction" (CD) as used above and below denotes the direction which is essentially normal to the machine direction.

The continuous web 1 may comprise only one material and exhibit a uniform construction in CD, but it preferably exhibits a sequence of two or more zones having different properties in CD whereby such zones preferably continuously extend in MD.

The term "zone" as used above and below refers to a section of the continuous web 1 in CD exhibiting an essentially uniform construction and/or uniform properties. The different zones can be formed by different materials which are joined to each other, for example, by adhesive means such as pressure-sensitive adhesive means, ultrasonic bonding, thermal bonding, mechanical bonding, stitching or any combination of these bonding methods. It is, however, also possible that different zones are created by "activating" one or more zones of the web. As used above and below, the term "activating" means subjecting the continuous web 1, for example, to a mechanical thermal, electrical and/or chemical treatment in order to impart different functionalities to the treated zones of the web.

The different zones may consist essentially of one material but it is also possible that the zones comprise a sequence of two or more layers of materials and/or exhibit substructures in the direction normal to the major surfaces 1a, 1b of the continuous web.

One or more zones of the continuous web 1 preferably comprise a backing or carrier film in order to impart structural integrity and/or stiffness to the web 1 in CD. The backing or carrier film may be selected from a variety of films or sheetings including single- or multilayered films, coextruded films, laterally laminated films or films comprising foam layers. The layers of such films or sheetings may comprise various materials such, as for example, polypropylene, polyvinylchloride, polyethylene terepthalate, polyethylene, polyolefin copolymers or blends of polyolefins such as, for example, a blend of polypropylene, LPDE (low density polyethylene) and/or LLDPE (linear low density polyethylene), textiles, and non-woven and foamed materials. The thickness of the backing is preferably between 30 and 500 µm and more preferably between 40 and 150 µm. The base weight of the backing is preferably between 20 and 500 $g/m^2$, more preferably between 40 and 300 $g/m^2$ and especially preferably between 40-200 $g/m^2$.

One or more zones of the continuous web 1 preferably comprise one or more elastically extensible materials extending in at least one direction when a force is applied and returning to approximately their original dimension after the force is removed.

Elastically extensible materials which are useful in the present invention include materials which preferably are elastically extensible without requiring an activation step. Such materials include elastic, natural or synthetic rubber, rubber foams, elastomeric scrims, woven or non-woven elastomeric webs, elastomeric composites, zero-strain stretch laminates or prestrained stretch laminates.

The elastically extensible materials may be made from a group of materials comprising essentially isotropic or essentially anisotropic materials, respectively. Useful elastic materials preferably exhibit an elongation at break as measured according to ASTM D 882 in the preferred direction of stretchability of at least 25% or more and, more preferably, of more than 50% and most preferably of more than 100%.

Preferred essentially isotropically elastic materials include elastomeric polyurethane materials, or natural or synthetic rubber materials such as, for example, ethylene-propylene-diene copolymers (EPDM), styrene-butadiene-styrene block copolymers (SBS) or styrene-(ethylene-butylene)-styrene block copolymers (SEBS). Elastomeric materials of the A-B or A-B-A block copolymer type which are useful in the present invention, include, for example, those described in U.S. Pat. No. 3,265,765, U.S. Pat. No. 3,562,356, U.S. Pat. No. 3,700,633, U.S. Pat. No. 4,116,917 and U.S. Pat. No. 4,156,673. Other elastomeric materials which may be used to form the elastic means include elastomeric polyamide materials and elastomeric polyolefin and polyester materials. Blends of these elastomers with each other or with modifying non-elastomers are also contemplated. For example, up to 50 wt. %, but preferably less than 30 wt. % with respect to the mass of the elastomeric material can be added as stiffening aids such as polyvinyistyrenes, polystyrenes, polyesters, epoxies, polyolefins or coumarone-indene resin. These stiffening aids tend to improve the flexibility of the elasomeric materials.

Preferred elastic materials are commercially available from Exxon Mobil Corp. under the trademark Vector and from Kraton Polymers Comp. under the trademark Kraton.

Additionally or alternatively it is also possible to subject one or more zones of the continuous web 1 to an activation treatment in order to render such zones elastically extensible and/or to increase such elastic extensibility, respectively. Preferred activation treatments include, for example, ring rolling, embossing, thermoforming, high pressure hydraulic forming or casting. Elastomeric laminates comprising at least one non-elastomeric skin layer and at least one core layer where the laminate is treated to exhibit preferential activation regions and non-preferential activation regions so that the preferential activation regions can be stretched to an elastic state, is disclosed in EP 0,521,388. This elastomeric laminate is useful in the present invention whereby the fastener portions 2 are preferably adhered to the non-preferential regions.

The continuous web 1 may comprise further materials such as, for example, stiffening materials, adhesive coatings and release materials such as release coatings or release tapes, coloured films, printings or registered marks. The continuous web 1 may also impart further functionalities such as breathability or differential stiffnesses to the continuous web 1. In case adhesive type fastening means are used printed release coatings may applied to part of the surface of the continuous web 1.

Stiffening materials include, for example, thermally or sonically structured surfaces or additional layers or coatings applied to the continuous web 1.

The continuous web 1 and, optionally, further components attached to it, preferably has a Gurley stiffness value both in CD and MD as evaluated according to TAPPI Standard Test T 543 om-94, of less than about 1,000 milligrams (mg) in an area of said continuous web including the fastening portion 2, i.e. after the fastening portion 2 has been assembled to the continuous web 1 as described below. The Gurley stiffness both in CD and MD preferably is less than 500 mg and especially preferably less than 200 mg.

The process of the present invention further includes providing fastening portions 2 which may be continuous or form individual, single patches.

The fastening portion 2 comprises a fastening means 3 which may be provided by adhesive fastening means, by mechanical fastening means, and/or by other male/female fastening means.

The adhesive of adhesive type fastening means 3 may be selected from a group of adhesives comprising hot-melt adhesives, UV- or thermally curable adhesives or pressure-sensitive adhesives. Pressure-sensitive adhesives are preferably selected from (meth)acrylate and/or natural or synthetic rubber based pressure-sensitive adhesives. Rubber-resin adhesives preferably comprise in addition to the rubber materials one or more tackifying resin in order to render the rubber materials tacky. Preferred examples of rubber-based pressure-sensitive adhesives are the polystyrene-polyisoprene block copolymers tackified with synthetic polyterpene resins. Suitable acrylate-based pressure-sensitive adhesives are disclosed, for example, in U.S. Re 24,906 or U.S. Pat. No. 4,710,536.

Fastening portions 2 comprising mechanical fastening means 3 preferably form part of a mechanical closure system comprising at least two interlocking, releasably engageable fastening means, one of them being a hook (or male) fastening means and the other being a loop (or female) fastening means. One of the fastening means of the mechanical closure system forms the fastening means 3 of the closure component 7 of the present invention, and the one or more further fastening means of the closure system are attached to other parts of the absorbent article like, for example, to the landing zone 14 of a diaper 10, so that such article can be secured, for example, to the body of the wearer.

A preferred mechanical fastening portion 2 comprises a base and a plurality of engageable fastening elements forming fastening means 3. In case of hook-type fastening means 3, the fastening elements usually comprise a stem supported at the base of the fastening portion 2 and an enlarged section which is positioned at the end of the stem opposite of the base. The enlarged section may have any shape such as hooks, T's, essentially flat discs, mushroom heads, or any other shape allowing for engagement with the corresponding loop fastening elements.

Mechanical fastening portions 2 comprising hook-type fastening means can be manufactured from a wide range of materials including nylon, polyester, polyolefins or any combination of these. Hook-type fastening portions which are useful in the present invention are disclosed, for example, in U.S. Pat. No. 4,894,060, U.S. Pat. No. 5,077,870 and U.S. Pat. No. 5,679,302. Preferred hook-type fastener portions 2 are commercially available from 3M Comp., St. Paul, Minn., U.S.A.

In case of loop-type fastening means 3, the fastening elements are usually formed by woven or non-woven fabrics or any other suitable material which interlocks with the corresponding hook fastening elements. Loop-type mechanical fastener portions include, for example, fiber loops projecting from a knitted, woven or non-woven backing or extrusion-bonded, adhesive-bonded and/or sonically-bonded fiber loops. Suitable loop-type fastening portions 2 comprising knitted or extrusion-bonded fastening means are commercially available, for example, from 3M Comp., St. Paul, Minn., U.S.A.

Fastening portions 2 comprising mechanical fastening means preferably comprise a base or backing bearing fastening elements on one of its surfaces and an adhesive layer on the opposite surface. The fastening means 2 is then attached to the continuous web 1 via such adhesive layer. The base or backing may be selected from a variety of polymeric films or sheetings, sheetings of paper and other woven or non-woven fibrous materials or metal film. The adhesive layer preferably comprises hot-melt adhesives or pressure-sensitive adhesives which are preferably selected from (meth)acrylate and/or natural or synthetic rubber based pressure-sensitive adhesives. The fastening portion 2 can also be thermally, mechanically or ultrasonically bonded to the continuous web 1.

The fastening means 3 of the fastening portion 2 and the inner and/or outer surface 1a, 1b of the continuous web of a material 1 are selected so that they releasably engage upon folding over flap 5 obtained by applying cuts 4 around at least part of the fastening portion 2 as is described in detail below.

The term "releasable engagement" means that the flap 5 when folded over onto the corresponding target surface 1a, 1b of the base 7a of the closure component interacts sufficiently strong with such surface so that the flap 5 is deactivated, i.e. essentially rendered immobile during processing and does not pop open during processing. The interaction must be, however, not too strong so that the flap can be releasably activated, i.e. unfolded, when the absorbent article is used and applied, for example, to the wearer. It may be desirable that the flaps 5 upon folding over are subjected to an additional pressing step in order to provide a secure releasable engagement. This can be obtained, for example, by passing the continuous web 1 bearing the flaps in the folded-over state between two rotatable nip rollers. Using an additional pressing down step is often desirable in case of mechanical fastener portions 2.

The term "releasable engagement" quantitatively means that the fastening means 3 preferably exhibits a 180° T-peel adhesion of not more than 2 N/inch from the inner and/or outer surface 1a, 1b of the continuous web 1 which the fastening means 3 contacts upon folding-over of said flap 5. The 180° T-peel adhesion which is measured according to ASTM-5170-91 is preferably not more than 2 N/inch, more preferably below 1.5 N/inch and especially preferably below 1 N/inch. The 180° T-peel adhesion preferably is higher than 0.1 N/inch and more preferably higher than 0.2 N/inch to secure adequate bonding of the flap 5 to the base 7a of closure component 7 during processing. Because of this releasable engagement the flap 5 bearing the fastening portion 2 is releasably secured to the continuous web 1 during the process of manufacturing of the closure components and does not pop open. This allows to run such process of manufacturing with high reliability and at high speeds and therefore to reduce manufacturing costs without damaging the fastening portions 2 and/or the manufacturing equipment.

If the flap 5 would not be brought into releasable engagement with the corresponding target surface 1a, 1b of the base 7a of closure component 7 the flap 5 could possibly engage to the opposite surface 1a, 1b of such target surface. This could significantly reduce the attainable speed of the manufacturing process or could even stop such process.

If the fastening portion 2 comprises a hook-type fastening means, the portion of the inner or outer surface of the web which comes into contact with the hook-type fastening means upon folding-over of the flap 5, preferably comprises a woven or non-woven fibrous material and/or loop fastening elements. Likewise, in case the fastening portion 2 comprises a loop-type fastening means 3, the corresponding portion of the inner or outer surface of the continuous web preferably comprises hook-type fastening elements. If the fastening portion 2 comprises an adhesive-type fastening means 3, at least the portion of the inner or outer surface of the continuous web 1 which comes into contact with the adhesive fastening means upon folding-over of flap 5 preferably exhibits a low surface energy. Such surface portion of the continuous web preferably is release-treated and, in particular, siliconized. It is also possible that the full surface of the continuous web is release-treated.

The fastening portion 2 may be provided continuously by unwinding it, for example, from a storage roll 22 and by subsequently continuously applying it to the continuous web of a material 1. It is also possible that the fastening portion 2 is provided continuously but cut into single, individual patches which are applied individually to the continuous web. It is furthermore also possible that the fastening portion 2 is provided discontinuously in the form of separate, individual patches which are temporarily attached, for example, to an auxiliary web. The separate, individual patches of the fastening portion are then secured to the continuous web 1, and the auxiliary web is wound up.

It is often preferred that the fastening portion is supplied continuously but attached discontinuously, i. e. that the continuous fastening portion is cut into separate, single segments prior to their application to the web. This technique avoids creating of additional waste because an auxiliary carrier web is not required, and it facilitates cutting of the flaps 5 because the simultaneous cutting of both the continuous web 1 and the fastening portion 2 is avoided.

The fastening portions 2 are applied to the continuous web 1 so that the fastening means 3 representing the plurality of fastening elements are exposed.

The fastening portions 2 can be applied to one or to both of the outer major or inner major surface 1a, 1b, respectively, of the continuous web of a material 1. The fastening portions 2 can also be arranged in various configurations on the continuous web including symmetrical or non-symmetrical, staggered or parallel or other configurations. The specific configuration chosen depends on various factors such as the size and symmetry of the closure components 7 to be manufactured, the tolerable amount of waste and the further processability of the closure components.

Figure 1:
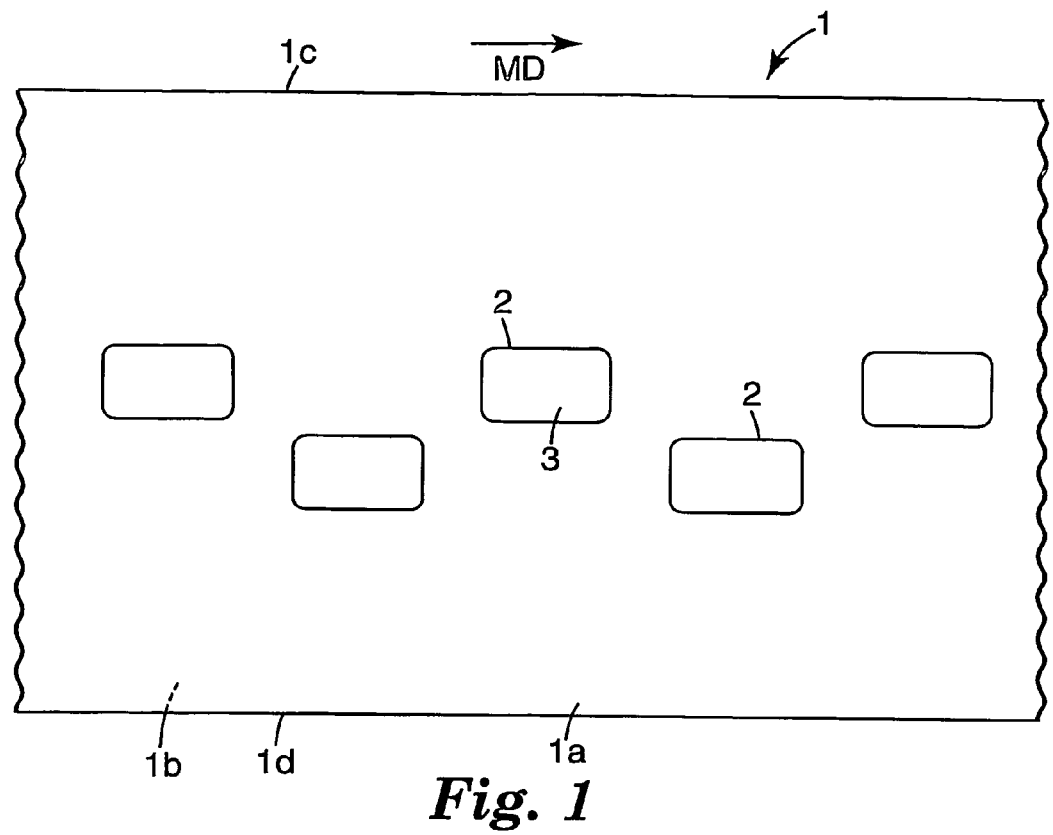
FIG. 1 schematically shows the inner surface 1a of a continuous web of a material 1 bearing discrete fastening portions 2 in a staggered configuration.

In the specific embodiment of FIG. 1, for example, the fastening portions are arranged on one surface of the continuous web in a staggered configuration along the centerline of the continuous web 1 in MD. The cuts 4 introduced into the continuous web 1 (see FIG. 2) and the subsequent folding-over of the flaps 5 (see FIG. 3) results in two continuous sub-webs of closure components 7 (one of which is shown in FIG. 4b). The closure components 7 of both sub-webs are symmetrical and of an identical shape. Since the two sub-webs are arranged with respect to each other at a rotation angle of 180°, the closure components 7 of the two sub-webs can be directly applied without any further rotation to different sides of the rear waistband portion 13 of a diaper as shown in FIG. 5, for example. The waste generated during this process of manufacturing which is represented by the bridges 6, 6', is minimal.

Thus, in view of the properties of the closure components 7 to be generated in the specific process schematically shown in FIG. 1-4a, 4b, it is advantageous to apply the fastening portions 2 in a staggered configuration onto one surface 1a, 1b of the continuous web 1 only.

Figure 10:
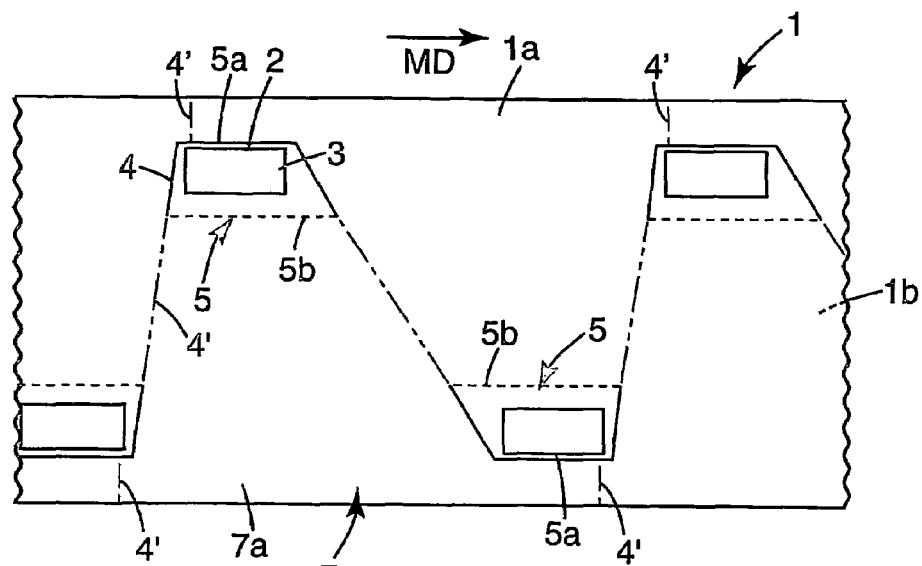
FIG. 10 schematically shows the continuous web 1 of a material bearing discrete fastening portions 2 arranged in a staggered configuration whereby adjacent fastening portions are joined to different surfaces 1a and 1b of the continuous web. The flaps 5 defined by cuts 4 (shown in solid bold lines) which each have a top edge 5a and a baseline 5b, are not yet folded over. Subsequent to such folding-over step, cuts 4' can be applied to provide separate, single closure components 7.

Contrary to this it is advantageous, for example, in the specific embodiment shown in FIG. 10 to apply fastening portions 2 subsequent to each other in MD, in an alternating fashion to the inner and outer major surfaces 1a, 1b, respectively, of the continuous web 1. If the fastening portions 2 were applied to one surface of the continuous web 1 only, the resulting non-symmetrical closure components 7 could only be applied to one side of the rear waistband section. By applying subsequent fastening portions 2 to different surfaces of the continuous web 1 in an alternating fashion, a continuous web 1 of non-symmetrical closure components 7 is obtained which can alternately be applied to the right and left side, respectively, of the rear waistband section 13. It should also be noted that the process of manufacturing shown in FIG. 10 does not generate any waste.

It is clear from these specific embodiments which were described to exemplify the invention without limiting it, that the specific configuration of the fastening portions 2 has to be selected and optimized in each case with respect to the shape and dimensions of the closure components 7 and their desired attachability to one or both sides of the rear waistband section 13 to be manufactured and the requirements of the process such as the tolerable amount of waste. Processes according to the present invention are preferred where the fastener portions 2 and their respective positioning on the continuous web 1, and the cuts 4,4',4" are selected to provide a multitude of pairs of a first and a second closure component 7 so that one of such closure components can be attached to the right and the other to the left side of the rear waistband portion of a diaper, respectively.

It is generally desirable that the surface coverage of the fastening portions 2 which is defined as the ratio of the sum of the areas of the fastening portions over the area of the continuous web is between 0.001 and 0.25 and more preferably between 0.025 and 0.175.

The fastening portion 2 can be adhered to the continuous web 1, for example, by adhesive means such as pressure-sensitive adhesive means, hot-melt adhesives or other adhesives, by ultrasonic bonding, thermal bonding and/or mechanical bonding. The adhesive means and/or the bonding conditions are preferably selected so that the fastening portion 2 is strongly bonded to the continuous web 1 and cannot be removed from such web without irreversibly deforming and/or damaging the continuous web 1 and/or the fastener portion.

In the next step, the continuous web 1 and, optionally, further components attached to it are cut to provide foldable flaps 5. The term "cut" 4 as used above and below includes full slits or cuts fully separating two adjacent portions of the continuous web 1 and, optionally, further components attached to it, and also intermittently arranged slits or cuts, perforations and the like. Full cuts 4 are preferred. The term "flap" is used above and below to denote a section of the continuous web 1 which is partly separated from the surrounding continuous web 1 by one or more cuts 4 and which is still partly connected to the surrounding continuous web 1 and/or a continuous sub-web obtained from it, respectively, at least through its baseline 5b. The separated part of the flap 5 can be folded over along the baseline 5b towards the surrounding continuous web 1 whereby in case of perforations or intermittently arranged cuts, the remaining connections between the flap 5 and the adjacent portions of the continuous web 1 need to be broken. The cuts 4 providing the flaps 5 preferably are discontinuous in MD and CD, i.e. they do not destroy the integrity of the continuous web 1 in CD or MD, respectively. Discontinuous cuts 4 are shown, for example, in FIGS. 2 and 3 where the cuts discontinuously extend around the fastening portion 2 but do not extend continuously in CD or MD, respectively. The integrity of the continuous web 1 is maintained, for example, in FIG. 3 via the bridges 6. It was found that folding over of the flaps 5 is facilitated in particular, under high speed processing conditions when the continuous web 1 is maintained in a connected, i.e. integral state in CD and MD prior to the folding over step.

The baseline 5b which thus essentially forms a rotation axis for the separated part of the flap 5, preferably is a straight line. The extension of the baseline 5b can vary and can be reduced so that the baseline 5b has, for example, a length of 1 mm only. The extension of the baseline 5b should be selected, however, so that the separated part of the flap 5 is reliably secured to the surrounding part of the web 1 and so that such separated part of the flap 5 can be rotated around such baseline without being separated from the surrounding part of the web 1.

The separated part of the flap 5 and the surrounding continuous web 1 can be separated by one or more cuts 4 which are arranged so that the separable part comprises at least part of the fastening portion 2. The cut or cuts 4 can form essentially straight lines but they can be of any shape and exhibit, for example, a convexly or concavely curved shape or exhibit, for example, a wavy substructure.

The cut line of the separated part of the flap 5 which is essentially opposite to the baseline 5b is denoted above and below as top edge 5a of the flap 5. The top edge 5a can have any shape and may be represented, for example, by a straight or a convexly and/or concavely curved line, by two or more straight and/or curved lines intersecting with each other or it may include, for example, a wavy or sawtooth-like substructure.

The baseline 5b preferably is essentially parallel with one of the longitudinal edges 1c, 1d of the continuous web 1 so that the flap 5 is rotated upon folding essentially into CD. It is also possible, however, that the baseline 5b forms an angle with respect to the longitudinal edges 1c, 1d of the continuous web 1 so that the flap 5 is rotated upon folding along the baseline 5b essentially under such angle with respect to CD.

Irrespective of whether the baseline 5b is essentially parallel to a longitudinal edge 1c, 1d of the continuous web 1 or forms an angle with such longitudinal edge 1c, 1d, such baseline 5b is referred to as facing the longitudinal edge 1c, 1d which is closest to it.

The method according to the present invention provides at least two flaps 5 along the extension of the continuous web in MD which are facing opposite longitudinal edges 1c, 1d of the continuous web 1. It was found by the present inventor that the waste generated during the manufacture of closure components can be minimized if the longitudinal web 1 comprises in MD at least one flap 5 facing the right longitudinal edge 1d and at least one flap facing the left longitudinal edge 1c, respectively.

The flap density is measured along the extension of the continuous web 1 in MD as the number of flaps per length unit. The overall flap density preferably is between 3/m and 300/m and more preferably between 5/m and 150/m.

The flap density of the flaps 5 which are facing the right longitudinal edge and the flap density of the flaps which are facing the left longitudinal edge, preferably deviate from each other by less than 50%, more preferably by not more than 40% and especially preferably by not more than 30% with respect to the lower value of the right and left flap density, respectively.

The length of the flap 5 in CD and/or normal to the baseline 5b, respectively, is defined by the distance between the baseline 5b and the top edge 5a of the flap 5. If the baseline 5b and the top edge 5a are not parallel to each other and/or if the top edge 5a is not linear, the maximum value of such distance is reported as the length of the flap 5 in CD and/or normal to the baseline 5b. Such length preferably is at least 10 mm, more preferably at least 15 mm and especially preferably at least 20 mm. The length of the flap preferably is between 25 mm and 250 mm, more preferably between 30 and 150 mm and especially preferably between 35 and 100 mm.

The shape and extension of the one or more cuts 4 and the shape and extension of the baseline 5b of the flaps 5 essentially determine the size and the shape of the flaps 5.

The flaps 5 can be symmetrical or non-symmetrical, respectively, for example, with respect to a direction normal to the baseline 5b. The width of the flap is defined as the extension of the flap in MD or in a direction parallel to the baseline 5b if the baseline is not parallel to the longitudinal edge of the continuous web whereby such extension is measured at about half of the height of the flap. The width of the flap 5 preferably varies between 8 and 200 mm, more preferably between 10 and 180 mm and especially preferably between 12 and 150 mm.

The size and shape of the flap 5 is selected so that it comprises at least part of the fastening portion 2. If such fastening portion 2 comprises a plurality of individual, single patches each flap may comprise one or more and, preferably, one, of such individual patches or fastening portion 2.

If the fastening portion 2 forms a continuous web applied to the continuous web 1 of a material in MD, the fastening portions 2 on the different flaps 5 are cut along with the continuous web 1 and, optionally, further materials attached to the continuous web 1, during the cutting step.

The cut or cuts 4, respectively, can be applied to the continuous web 1 so that the fastening portion 2 is located essentially in the center of the flap, i. e. the distance between the top edge 5a of the flap 5 and the center of the fastening portion 2 essentially equals the distance between the baseline 5b of the flap and the center of the fastening portion 2. It is also possible that the cut or cuts 4 are applied to the continuous web so that the fastening portion does not have a centered position with respect to the flap 5. In this case it is preferred that the distance between the top edge 5a of the flap and the center of the fastening portion 2 is between 0.05 and 0.8 and more preferably between 0.1 and 0.7 of the distance between the baseline 5b and the center of the fastener portion.

Although it is possible that the fastening portion essentially extends to the top edge 5a of the flap 5 it is preferred that there is a distance between the top edge 5a of the flap and the edge of the fastening portion 2 facing such top edge 5a. This construction provides a soft-edge finger-lift between the top edge 5a and the edge of the fastening portion facing the top edge 5a which facilitates gripping and unfolding of the flap 5. The fingerlift preferably has a length, i.e. an extension in CD and/or along a direction normal to the baseline 5b of the flap, of at least 1 mm, more preferably of at least 2 mm and especially preferably of at least 3 mm.

The flaps 5 are then folded over in the next step in a direction essentially normal to the baseline 5b so that the fastening elements of the fastening portion 2 are brought into contact and releasably engage with the continuous web 1 between the baseline 5b and the longitudinal edge 1c, 1d such baseline is facing.

The part of the continuous web 1 upon which the fastening portion 2 is folded and with which it releasably engages, forms the base 7a of the closure component 7. The individual closure components 7 are obtained from the continuous web by applying additional cuts 4', 4". The cuts 4',4" can be full slits or cuts but intermittently arranged slits or cuts, perforations and the like can also be used. The cuts 4',4" can be used to break down the continuous web 1 into continuous sub-webs, and/or they can also be used to provide single separated closure components 7. The cuts 4' applied in FIG. 4a, for example, provide two separate sub-webs one of which is shown in FIG. 4b. Single separated closure components 7 are then obtained from the sub-web of FIG. 4b by applying additional cuts 4".

Figure 4A:
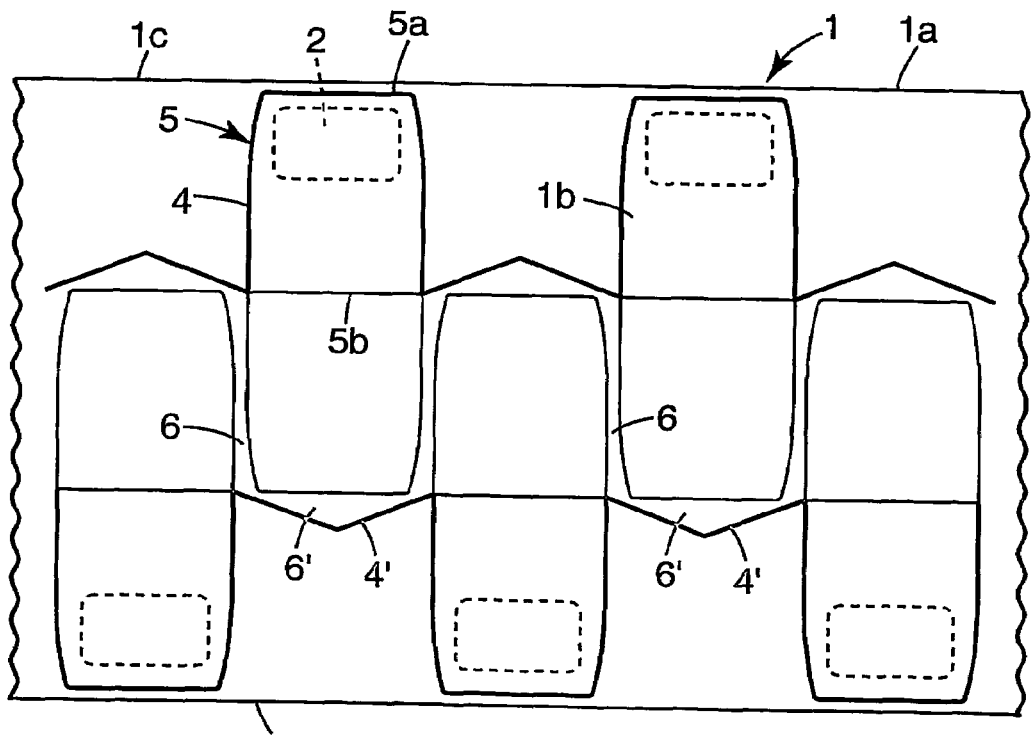
FIG. 4a schematically shows the continuous web 1 of a material of FIG. 3 wherein additional cuts 4' have been applied thereby separating the web 1 into two separate continuous sub-webs from which a sequence of closure components 7 (shown in FIG. 4b) can be cut.

The cuts 4',4" can be continuous or discontinuous The cuts 4' applied in FIG. 4a, for example, are discontinuous in MD and extend between adjacent flaps 5 facing one edge of the continuous web whereas the cuts 4" applied in FIG. 4b are continuous in CD of the sub-web and provide separated single closure components 7.

The cuts 4', 4" applied are selected so that the closure component 7 comprises at least one flap 5. The closure component 7 may comprise, for example, two flaps 5, 5' which may be of identical or different shape. The two baselines 5b, 5b' of such flaps 5,5' may be arranged in one line or they may be offset with respect to each other. In contrast to the prior art methods for providing closure components such as those disclosed in U.S. Pat. No. 5,759,317 the method of the present invention is very versatile and allows, for example, for the production of flaps 5 of various shapes and of closure components having more than one flap 5.

Using two or more flaps 5 per closure component 7 may be especially advantageous in adult incontinence articles where the base 7a of the closure component may be large.

In baby diapers 10 it is generally preferred for cost reasons that the closure component comprises one flap 5 only.

The cuts 4,4',4" applied in the method of the present invention are selected so that the waste w generated during the manufacture of the closure components 7 which is defined as 1−(sum of surface area of the closure components with the flaps being in an unfolded position/surface area of the continuous web)

is less than 0.2. The waste w preferably is less than 10%, more preferably less than 7.5%, especially preferably less than 5% and most preferably less than 2%.

This minimization of waste is obtained by providing at least two flaps 5 along the extension of the continuous web 1 in MD which are facing opposite longitudinal edges 1c, 1d of the continuous web 1 and by appropriately applying cuts 4,4',4".

The specific embodiments of the present invention illustrated in FIG. 1-12 below give ample guidance how minimization of waste can be achieved by appropriately selecting cuts 4,4' and 4". In FIG. 4a, the waste generated is represented by bridges 6,6'. While a small amount of waste is also generated in the embodiments of FIGS. 8 and 11, no waste is generated in the embodiment of FIG. 10 at all.

The height of the closure component 7 comprising the flap 5 in its folded state is typically given by the distance between the baseline 5b of the flap 5 and the baseline of base 7a which usually corresponds to the longitudinal edge 1c, 1d of the continuous web 1 such baseline 5b faces. The baseline of the base 7a of the closure component 7 represents the boundary line of the base 7a in CD. The height of the basis 7a of the closure component 7 is selected so that at least part of the fastening elements of the fastening portion 2 releasably engages with the surface of the continuous web 1 upon folding over. The top edge 5a of the flap 5 may exceed beyond the corresponding longitudinal edge 1c, 1d upon folding over to an extent that the fastening elements of the fastening portion 2 still releasably engage with the continuous web 1. In this embodiment the height of the flap 5 is larger than the height of the base 7a of the closure component 7. In another embodiment which is also preferred, the height of the flap 5 is smaller than the height of the base 7a of the closure component 7. The ratio of the height of the flap 5 and the height of the closure component 7 preferably varies between 0.05 and 2 and more preferably between 0.1 and 1.5.

Depending on the height of the base 7a of the closure component 7, one or more closure components 7 can be obtained in the CD of the continuous web 1. If the closure component 7 essentially extends over the width of the continuous web 1 in CD so that only one closure component 7 is obtained in CD (see, for example, FIG. 10), the continuous web may be wound into a stable roll for storage. If the continuous web 1 comprises along its width in CD more than one closure component 7 as exemplified in FIG. 4a,b or FIGS. 8 and 9, two or more continuous sub-webs may be obtained upon cutting (see, for example, FIG. 4b) which each may be wound up into stable rolls for storing. Alternatively, prior to winding the sub-webs for storage, the bridges 6,6' which may still be present between the sub-webs to form an integral web 1, can be weakened by introducing, for example, perforations into such bridges. The bridges connecting, for example, the two sub-webs of FIG. 4a are denoted therein with the reference number 6. After introducing such perforations the continuous web 1 can be rolled up and stored. The sub-webs can then be obtained by merely unwinding the roll and separating the continuous web 1 by tearing it in CD thereby breaking said perforations. This eliminates one cutting operation on high speed manufacturing lines such as manufacturing lines for disposable diapers. This configuration of the roll of the continuous web 1 also eliminates the need to inventory 'right hand' and left hand' rolls of the sub-webs as both are contained in one stable roll.

The individual closure components 7 can then be obtained by unwinding such rolls and cutting. A specific example of a continuous web 1 containing one closure component 7 in CD, is shown in FIG. 10. Alternatively, when the cuts 4', 4" are introduced as weakened lines such as perforations prior to winding up the roll for storage, the closure components 7 can be obtained by unwinding the rolls and tearing the web to break such perforations.

If the continuous web 1 comprises two or more closure components in CD, the continuous web 1 is preferably cut into continuous sub-webs first each of them comprising one closure component 7 in CD. This is exemplified in FIGS. 4a and 4b for a continuous web 1 comprising two closure components 7 in CD. The continuous sub-webs obtained upon cutting can each be wound into a stable roll for storage. One of the two sub-webs obtained from the continuous web 1 of FIG. 4a is shown in FIG. 4b. Each of the sub-webs can be wound up in single planetary or levelwinding format or may be festooned since the fastening means 3 of the fastening portions 2 are releasably engaged to the surface of the base 7a of the closure component, i.e. since the fastening means are temporarily deactivated. The individual closure components 7 can be obtained by unwinding the roll and cutting.

The width and shape of the base 7a of the closure component 7 can be varied broadly. The width of the base 7a, i. e. its extension in MD, can be less than the width of the closure component although this is usually not preferred. The width of the basis 7a of the closure component 7 can be distinctly greater than the width of the flap 5 to provide so-called "big ear"-type closure components 7. Closure components of this type provide both a closure system and an ear region to an absorbent article as is schematically illustrated for a diaper having an hour-glass shape, in FIGS. 5a and 5b. The ear-region partly overlaps with the front waistband portion 12 upon securing the diaper to the body of a wearer to provide a reliable and comfortable fit.

When using big-ear type closure components 7 the chassis of the diaper can have, for example, a rectangular shape which considerably facilitates manufacturing of the diaper.

The ratio of the width of the base 7a of the closure component 7 and the width of the flap 5 preferably is between 0.5 and 20, more preferably between 0.8 and 18 and especially preferably between 1 and 15.

Figure 9:
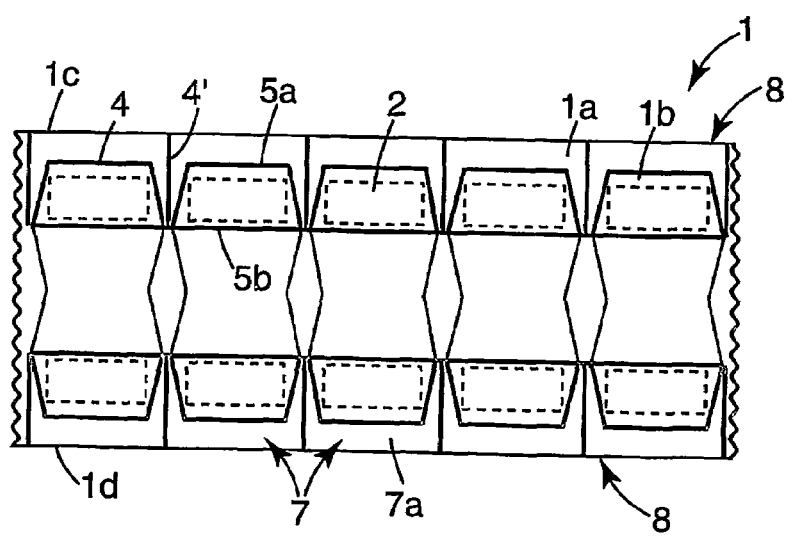
FIG. 9 schematically shows the web of FIG. 8 where the flaps 5 are folded over in cross-direction and additional cuts 4' have been applied to provide discrete closure components 7.

The shape of the base 7a of the closure component 7 can vary broadly and includes, for example, essentially rectangular or trapezoidal shapes shown in FIGS. 4b, 9 and 10.

In the first step of the method according to the present invention the fastening portion 2 and the continuous web 1 are provided, and the fastening portion 2 is fastened to the continuous web 1. Any method capable of bonding different materials together is considered suitable in the method of the present invention. The fastening portion 2 can be joined to the web 1, for example, by adhesive bonding, ultrasonic bonding, thermal bonding, mechanical bonding and/or stitching whereby bonding of the fastening portion 2 can be effected via part or all of the surface of the fastening portion which is opposite to the fastening means 3.

Cutting the web 1 in order to provide flaps 5 may be performed by using rotary cutters, air knives, thermal knives, pinch cutters, ultrasonic cutters or lasers. Folding-over of the flaps 5 around its baseline 5b onto the base 7a of the closure component 7 may be effected, for example, by using a sprocket wheel in conjunction with a folding bar or plows. If desired and/or necessary, the flaps 5 may subsequent to the folding step be pressed into contact with the surface of the base 7a of the closure component 7 in order to reliably engage the fastening elements of the fastening portion 2 with the surface of the base 7a of the closure component 7. This may be obtained, for example, by passing the web 1 comprising flaps 5 being folded over through a pair of rotatable nip rolls.

The resulting construction can then be wound up for storing, for example. The resulting construction can also be subjected to further cutting in order to provide sub-webs 8 and/or single closure components 7.

A specific example of the process of the present invention is described in some detail below in connection with FIG. 6.

In the process of the present invention, the fastening portion 2 of the flaps 5 is releasably engaged with the base 7a of the closure component 7 so that the flaps 5 do not pop open or flutter even at high manufacturing speeds. This could result in damaging the fastening portion 2, other parts of the absorbent article to be manufactured and/or the manufacturing equipment.

In addition to this, the process of the present invention provides a low or very low amount of waste. This is obtained by providing at least two flaps 5 along the extension of the continuous web 1 in MD which are facing opposite longitudinal edges 1c, 1d of the continuous web 1.

The invention will now be explained by referring to the specific embodiments of FIG. 1-10. These specific embodiments are to illustrate the invention without limiting it.

FIG. 1 shows a section of a continuous web 1 having two parallel longitudinal edges 1c (left edge in MD) and 1d (right edge in MD). Individual fastening portions 2 comprising fastening means 3 are applied discontinuously in a staggered configuration along the (hypothetical) centerline of the continuous web.

Figure 2:
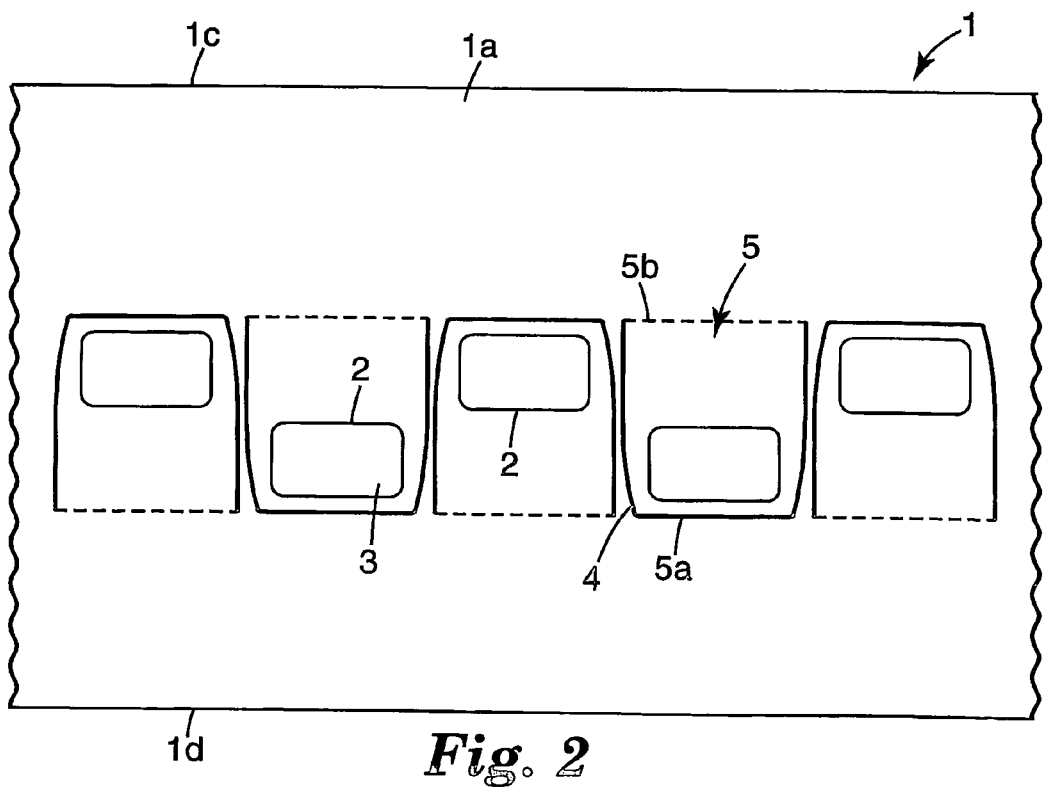
FIG. 2 schematically shows the continuous web of a material 1 of FIG. 1 additionally comprising cuts 4 around part of the fastening portions 2 thereby providing flaps 5 having a top edge 5a and a baseline 5b. The cuts 4 are shown in bold, and the baseline 5b is represented by broken lines depicted in bold.

In FIG. 2, cuts 4 have been applied around each fastening portion 2 to provide essentially rectangular flaps 5. The baseline 5b which is defined by the two end-points of the cut line 4, is essentially parallel to the respective longitudinal edge 1c, 1d such baseline 5b faces. The baselines 5b of two subsequent flaps 5 face opposite longitudinal edges 1c, 1d so that a sequence of flaps 5 is obtained which are foldable to opposite longitudinal edges in an alternating fashion.

The top edge 5a of the flap 5 which is essentially parallel to the baseline 5b exceeds the upper edge of the fastening portion 2 to provide a fingerlift.

Figure 3:
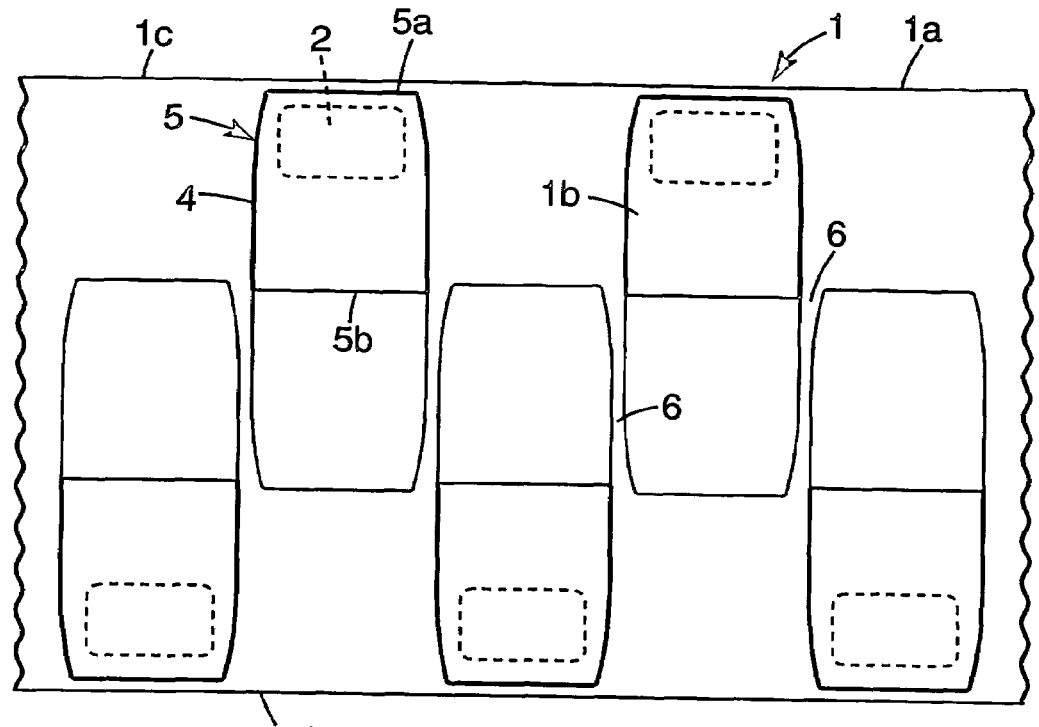
FIG. 3 schematically shows the continuous web of a material 1 of FIG. 2 wherein the flaps 5 have been folded over in cross-direction along their respective baselines 5b, the fastening portions 2 facing the inner surface 1a of the continuous web 1 of a material and the flaps 5 exposing part of the outer surface 1b of the continuous web 1 of a material. The circumference of the flap as folded over is shown in bold whereas the cut-away parts of the continuous web of a material 1 are indicated with weak lines. The fastening portions 2 which are attached to the inner side of the flaps 5 are shown in dotted lines.
Figure 4B:
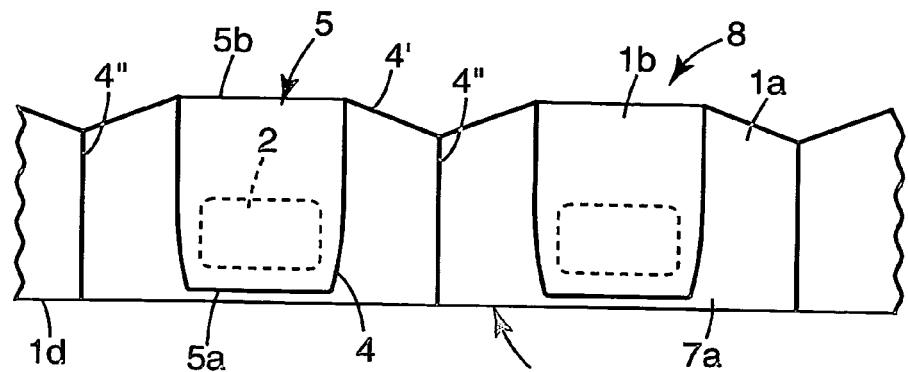
FIG. 4b schematically shows a sequence of separate, single closure components 7 which are obtained from one of the two separate continuous sub-webs of FIG. 4a by applying additional cuts 4".

The configuration of FIG. 3 has been obtained by folding over the flaps 5 of FIG. 2 to the corresponding longitudinal edges 1c, 1d. The fastening portions 2 which are shown in dotted lines are in contact with the surface 1a of the continuous web 1. The integrity of the continuous web 1 is maintained through the bridges 6 in the middle of the continuous web 1.

In FIG. 4a, the continuous web 1 of FIG. 3 is separated into two continuous sub-webs by means of cuts 4'. The cuts 4' are formed by two intersecting straight lines whereby the point of intersection defines the point of cutting for providing individual closure components 7 as can be seen in FIG. 4b. One of the two sub-webs which can be wound into stable rolls if desired, is shown in FIG. 4b. It is also possible, however, that the closure components 7 are cut and processed directly without an intermediate winding and storage step.

The waste generated during the process of manufacturing shown in FIG. 1-4a, 4b which is represented by bridges 6 and 6', is relatively small and tolerable.

FIG. 5 schematically shows the closure components 7 obtained in FIG. 4b being attached to a diaper 10. The diaper 10 essentially has an hour-glass shape and comprises a rear waistband section 13, a crotch section 15 and a front waistband section 12. The absorbent core 18 of the diaper 10 which is schematically indicated for purposes of demonstration only, is sandwiched between the top sheet 11 forming the inside of the diaper and the outer backsheet 17. The closure components 7 are secured to both lateral ends of the rear waistband portion 13 via seam sections 16. Bonding of the closure components 7 can be effected by various methods including, for example, adhesion bonding, ultrasonic bonding, thermal bonding or mechanical bonding. In FIG. 5a, the flap 5 is folded over to the base 7a of the closure component 7. The closure component 7 is obtained in this configuration in the process of the present invention as is shown in FIG. 4a, 4b. In FIG. 5b, the flap 5 has been folded back so that the fastening portion 2 is exposed. In this configuration, the fastening elements of the fastening portion can be engaged with the corresponding fastening elements of the landing zone 14 applied to the backsheet 17 of the diaper 10.

Figure 6:
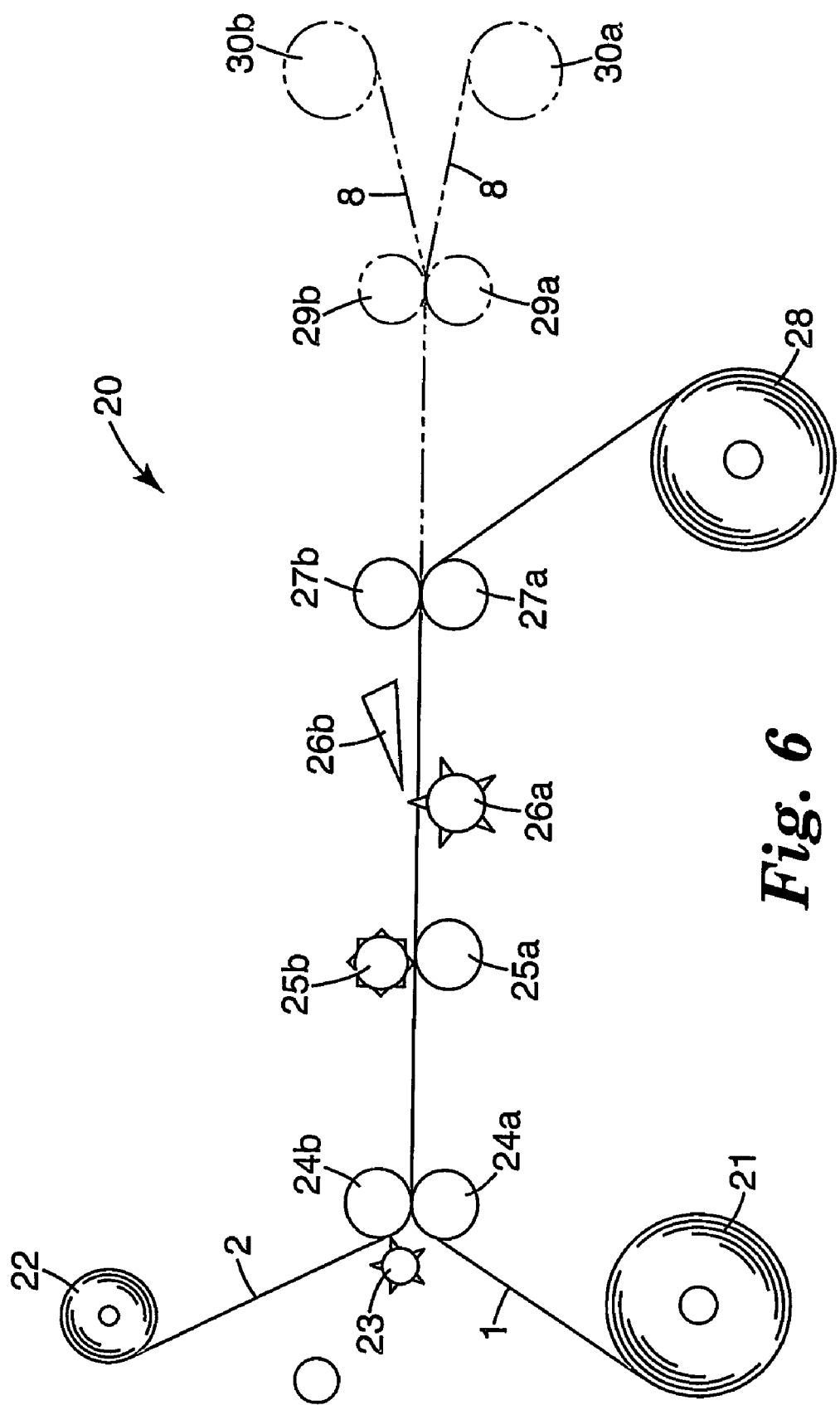
FIG. 6 schematically shows an apparatus suitable for manufacturing the closure components 7 of the present invention. The apparatus comprises a supply roll 21 of the continuous web 1 of a material, a supply roll 22 of the continuous fastening portion 2, cutting means 23 for supplying individual fastening portions 2, applicator means 24a, 24b comprising a vacuum roll 24b for attaching the fastening portions 2 to the web 1, a rotary cutting means 25a, 25b for providing flaps 5, a sprocket wheel 26a and a folding bar 26b folding over the flaps 5 in cross-direction, a pair of rollers 27a, 27b and a storage roll 28. The apparatus optionally further comprises an additional rotary cutting means 29a, 29b and two storage rolls 30a, 30b.

FIG. 6 schematically shows a method of manufacturing the closure components 7 of FIG. 4b and the corresponding equipment. The continuous web 1 of a material is unwound from supply roll 21 and fed into a lamination station 24a, 24b where individual patches of fastening portion 2 are laminated to the continuous web 1. The individual fastening portions are obtained by unwinding a continuous fastening portion 2 from supply roll 22 which is cut by cutting means 23. The individual, single patches of fastening portion 2 are bonded to the continuous web 1 by means of a pressure-sensitive adhesive which is attached to the base of the fastening portions 2. The individual patches of fastening portion 2 are held in place during lamination by vacuum roller 24b. The resulting continuous web 1 comprising individual fastening portions 2 is shown in FIG. 1.

The cuts 4 are applied around the fastening portion 2 through the continuous web 1 by the rotary cutting means 25a, 25b comprising a rotary cutting wheel 25b. The flaps 5 thus prepared which are shown in FIG. 2 are folded over by means of the sprocket wheel 26a in conjunction with sprocket wheel 26a and folding bar 26b. The resulting continuous web 1 comprising flaps 5 which are folded over, is shown in FIG. 3. This construction can be wound onto storage roll 28 and stored.

Alternatively, the continuous web 1 comprising flaps 5 being folded over as shown in FIG. 3 can be passed through rotary cutting means 29a, 29b to provide additional cuts 4' as shown in FIG. 4c. Because of these additional cuts 4' the construction of FIG. 4a is separated into two continuous sub-webs 8 from which individual closure components 7 can be cut. One of such sub-webs 8 is shown in FIG. 4b. The two sub-webs 8 of FIG. 4b can be wound onto storage rolls 30a, 30b and stored.

Figure 7:
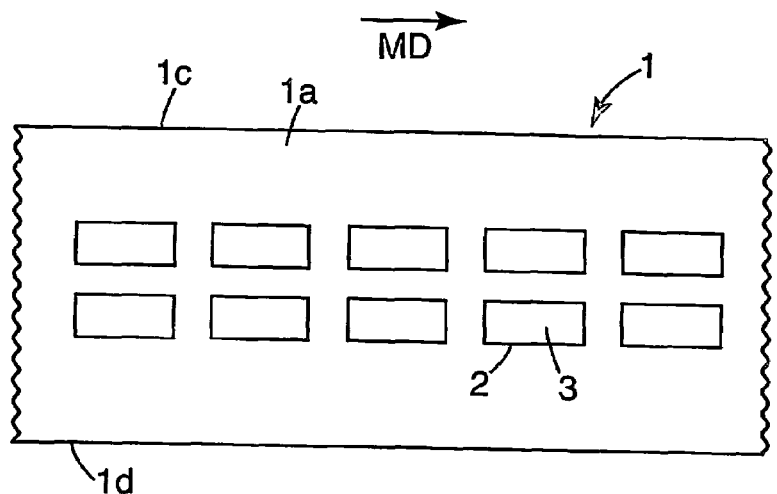
FIG. 7 schematically shows a continuous web 1 of a material bearing discrete fastening portions 2 arranged in a directly opposite configuration.

The continuous web 1 of FIG. 7 bears a plurality of individual patches of fastening portion 2 being arranged in pairs directly opposite to each other along the centerline of the continuous web 1. The individual patches of fastening portion 2 comprise fastening means 3.

Figure 8:
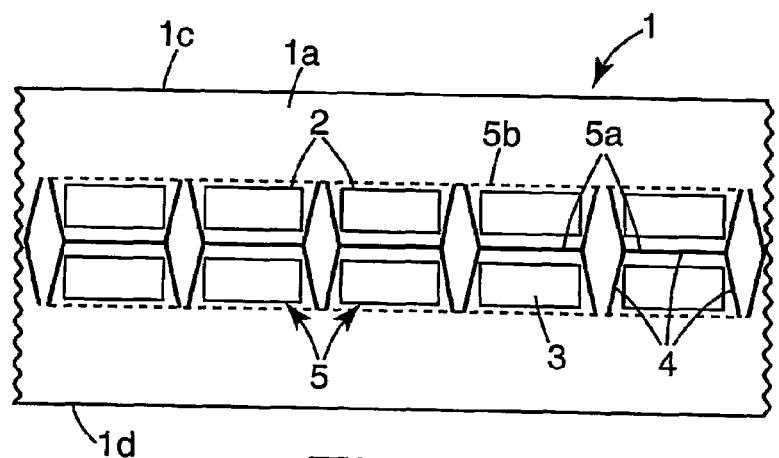
FIG. 8 schematically shows the web of FIG. 7 comprising cuts 4 around part of the fastening portions 2 thereby providing flaps 5, each having a top edge 5a and a baseline 5b.

FIG. 8 shows a plurality of flaps 5 which are obtained by applying cuts 4 around the individual patches of fastening portion 2. The flaps comprise a top edge 5a and a baseline 5b which is defined by the end points of the lateral cuts providing the sides of the flaps 5.

The flaps are folded around their baseline 5b towards the respective longitudinal edge 1c, 1d which is faced by such flaps 5 as is shown in FIG. 9. Individual closure components 7 can be cut from the two continuous sub-webs 8 of FIG. 9.

The individual closure components 7 which can be obtained from the sub-web 8 of FIG. 4b and FIG. 9, respectively, are symmetric. These symmetric individual closure components 7 can be applied, for example, to both lateral ends of the rear waistband section 13 as is schematically shown in FIG. 5.

Contrary to this, subsequent closure components 7 which can be cut from the continuous web 1 of FIG. 10 can be applied to different ends of the rear waistband section 13 only if the individual patches of fastening portion 2 are applied to different surfaces 1a, 1b of the continuous web. This results from the unsymmetrical shape of the closure components 7 of FIG. 10. The corresponding structure is shown in FIG. 10 where cuts 4 have been provided around the fastening portions 2 to provide flaps 5, the cuts 4 are indicated by solid bold lines. The flaps 5 thus obtained have not yet been folded over in FIG. 10, the further cuts 4' which are required to provide individual closure components 7 are shown in bold dot-dash lines. The waste generated when manufacturing the closure component 7 according to FIG. 10, is zero.

If the fastening portions 2 were applied in the construction of FIG. 10 only to one surface of the continuous web, the resulting closure components could only be used on one side of the rear waistband section 13 of diaper 10, for example. In this case, two different production runs would be required applying the fastening portion 2 in a first run, for example, to surface 1a and in the second run to the other surface 1b of the continuous web, respectively.

Figure 11:
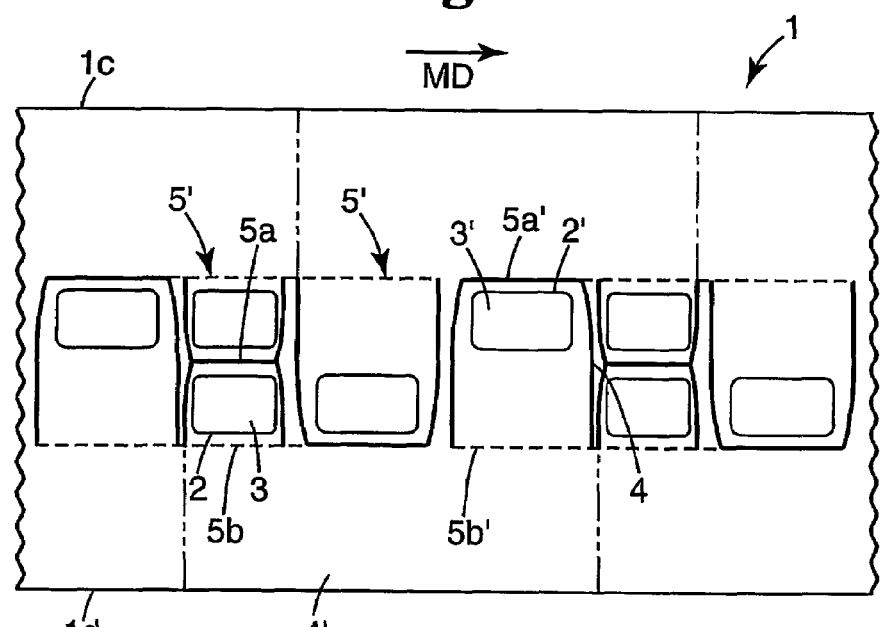
FIG. 11 schematically shows the continuous web 1 of a material bearing discrete fastening portions 2, 2' having a different size. The flaps 5, 5' defined by cuts 4 (shown in solid bold lines) which each have a top edge 5a, 5a' and a baseline 5b, 5b', are not yet folded over.

FIG. 11 schematically shows the continuous web 1 of a material bearing discrete fastening portions 2,2' having a different size. The smaller fastening portions 2 are arranged directly opposite to each other along the centreline of the continuous web in MD, and they separate two adjacent larger fastening portions 2' from each other. The larger fastening portions 2' are arranged along the centreline of the continuos web in MD in a staggered configuration with respect to each other.

The fastening portions 2,2' are arranged on flaps 5,5' which likewise are of a different size. The flaps 5,5' which are defined by cuts 4 (shown in bold lines) each have a top edge 5a, 5a' and a baseline 5b, 5b'.

The flaps shown in FIG. 11 have not yet been folded over. Subsequent to such folding over step, further cuts 4' are applied (shown in bold dash-dotted lines) to provide a plurality of individual closure components one of which being shown in FIG. 12.

Figure 12:
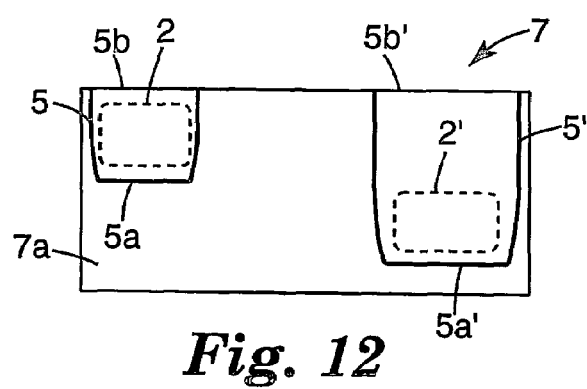
FIG. 12 schematically shows a single closure component 7 obtained from the continuous web 1 of FIG. 11 by applying cuts 4'.

The closure component 7 of FIG. 12 which comprises two flaps 5,5' and two fastening portions 2,2', is especially suited for use in adult absorbent articles such as adult incontinence products.

The invention claimed is:

1. A method of preparing closure components suitable for use in absorbent articles, comprising the steps of
    (a) providing a fastening portion comprising fastening means,
    (b) providing a continuous web of a material in a machine direction, said continuous web having a first outer major surface and a second inner major surface and a left and right longitudinal edge, at least one of said first and second major surfaces being capable of releasably engaging with the fastening means,
    (c) joining said fastening portion in the machine direction to at least one of the inner or outer major surfaces of the continuous web so that the fastening means of said fastening portion are exposed,
    (d) applying at least two first cuts to the continuous web in order to provide at least two flaps each having a top edge and a baseline, each of said at least two first cuts being discontinuous in the machine direction and in a cross direction such that the integrality of the continuous web is maintained, each of said at least two flaps bearing at least part of said fastening portions and being connected to the continuous web at least through its respective baseline so that the baseline of at least one of said at least two flaps is closer to the left longitudinal edge than the right longitudinal edge of the continuous web, and the baseline of at least one of said at least two flaps is closer to the right longitudinal edge than the left longitudinal edge of the continuous web, (e) folding over the flaps into a direction from their top edges to their baseline essentially along said base line onto the continuous web so that the fastening means releasably engage with the first outer major surface or the second inner major surface of the continuous web, wherein upon folding, the integrality of the continuous web is maintained, and (f) applying further cuts to the continuous web to produce individual closure components comprising said flaps in a folded position.

2. The method according to claim 1 wherein flaps subsequent to each other in the machine direction are folded over onto the continuous web alternately in opposite directions.

3. The method according to claim 1 wherein at least part of the continuous web has elastic properties.

4. The method according to claim 1 wherein at least part of the continuous web is stiffened.

5. The method according to claim 1 wherein the fastening portions are joined to the continuous web by adhesive means, by ultrasonic bonding, thermal bonding, mechanical bonding, stitching or any combination of these bonding methods.

6. The method according to claim 1 wherein at least two fastening portions are arranged on the continuous web in a directly opposite or staggered opposite configuration in cross-direction.

7. The method according to claim 1 wherein at least two fastening portions are provided, and wherein one of the at least two fastening portions is joined to the inner major surface and the other of the at least two fastening portions is bonded to the outer major surface of the continuous web.

8. The method according to claim 7 wherein the at least two fastening portions are subsequent to each other in the machine direction and are arranged alternately on the inner and outer surface, respectively, of the continuous web.

9. The method according to claim 1 wherein the top edge of the flap does not exceed the corresponding longitudinal edge of the continuous web.

10. The method according to claim 9 wherein the distance between the longitudinal edge of the continuous web and the top edge of the flap is at least 5% with respect to the height of the flap.

11. A method of preparing a stable roll comprising a sequence of pre-formed closure components suitable for use in absorbent articles, in machine direction, said method comprising the steps of (a) providing a fastening portion comprising fastening means, (b) providing a continuous web of a material in a machine direction, said continuous web having a first outer major surface and a second inner major surface and a left and right longitudinal edge, at least one of said first and second major surfaces being capable of releasably engaging with the fastening means, (c) joining said fastening portion in the machine direction to at least one of the inner or outer major surfaces of the continuous web so that the fastening means of said fastening portion are exposed, (d) applying at least two first cuts to the continuous web in order to provide at least two flaps each having a top edge and a baseline, each of said at least two first cuts being discontinuous in a machine direction and in a cross direction, each of said at least two flaps bearing at least part of said fastening portions and being connected to the continuous web at least through its respective baseline so that the baseline of at least one of said at least two flaps is closer to the left longitudinal edge than the right longitudinal edge of the continuous web, and the baseline of at least one of said at least two flaps is closer to the right longitudinal edge than the left longitudinal edge of the continuous web, (e) folding over the flaps into a direction from their top edges to their baseline essentially along said base line onto the continuous web so that the fastening means releasably engage with the first outer major surface or the second inner major surface of the continuous web, and subsequently (f) winding up the continuous web into a roll.

12. A stable roll comprising a sequence of pre-formed closure components, said roll comprising a continuous web of a material in a machine direction having a first outer major surface and a second inner major surface and a left and right longitudinal edge, said continuous web bearing fastening portions comprising fastening means and at least two flaps each having a top edge and a baseline, each of the flaps bearing at least part of said fastening portions and being connected to the continuous web at least through its respective baseline, so that the baseline of at least one of said at least two flaps is closer to the left longitudinal edge than the right longitudinal edge of the continuous web, and the baseline of at least one of said at least two flaps is closer to the right longitudinal edge than the left longitudinal edge of the continuous web, said flaps being folded over into a direction from their top edges to their baseline essentially along said baseline onto the continuous web so that the fastening means are in releasable engagement with the corresponding surface of the continuous web.

13. The stable roll according to claim 12 which comprises at least two closure components along the width of the continuous web in a cross direction arranged in two or more sub-webs in the machine direction whereby such sub-webs are connected to each other by bridges which can be separated upon unwinding to give two or more continuous sub-webs in the machine direction.

14. The stable roll according to claim 12, wherein the fastening portions comprise mechanical fastening means.

15. The method according to claim 11, wherein the fastening portion comprises mechanical fastening means.

16. The method according to claim 1, wherein the fastening portion comprises mechanical fastening means.

17. The method according to claim 1, wherein the first and further cuts are applied so that a waste defined by:

1−(sum of surface area of the closure components with the flaps being in an unfolded position/surface area of the continuous web)

is less than 0.2.

* * * * *

UNITED STATES PATENT AND TRADEMARK OFFICE
CERTIFICATE OF CORRECTION

PATENT NO. : 7,658,813 B2 Page 1 of 1
APPLICATION NO. : 10/545976
DATED : February 9, 2010
INVENTOR(S) : Johann F. Petersen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,658,813 B2 | Page 1 of 1 |
| APPLICATION NO. | : 10/545976 | |
| DATED | : February 9, 2010 | |
| INVENTOR(S) | : Johann Petersen | |

It is certified that error appears in the above-identified patent and that said Letters Patent is hereby corrected as shown below:

Column 5
Line 58, delete "mechanical" and insert -- mechanical, --, therefor.

Column 6
Line 53, delete "polyvinyistyrenes," and insert -- polyvinylstyrenes, --, therefor.

Signed and Sealed this
Tenth Day of May, 2011

David J. Kappos
*Director of the United States Patent and Trademark Office*